(12) United States Patent  
Bujas et al.

(10) Patent No.: US 7,178,384 B2
(45) Date of Patent: Feb. 20, 2007

(54) METHOD AND APPARATUS FOR MEASURING ULTRALOW PERMEATION

(75) Inventors: Roko S. Bujas, Leucadia, CA (US); Ralf Dunkel, San Diego, CA (US)

(73) Assignee: General Atomics, San Diego, CA (US)

( * ) Notice: Subject to any disclaimer, the term of this patent is extended or adjusted under 35 U.S.C. 154(b) by 231 days.

(21) Appl. No.: 10/772,765

(22) Filed: Feb. 4, 2004

(65) Prior Publication Data

US 2005/0167598 A1   Aug. 4, 2005

(51) Int. Cl.
*G01N 15/08* (2006.01)
(52) U.S. Cl. .......................................... 73/38
(58) Field of Classification Search .............. 73/38
See application file for complete search history.

(56) References Cited

U.S. PATENT DOCUMENTS

| | | | | |
|---|---|---|---|---|
| 3,286,509 A | | 11/1966 | Gluckman et al. | 73/38 |
| 3,498,110 A | * | 3/1970 | Brun | 73/38 |
| 3,580,067 A | * | 5/1971 | Mandrell et al. | 73/159 |
| 3,590,634 A | * | 7/1971 | Pasternak et al. | 73/38 |
| 3,937,649 A | | 2/1976 | Ridgely | 176/19 |
| 3,999,066 A | * | 12/1976 | Osborne et al. | 250/304 |
| 4,049,405 A | * | 9/1977 | Goldsmith et al. | 55/479 |
| 4,656,865 A | * | 4/1987 | Callan | 73/38 |
| 4,663,969 A | | 5/1987 | Bibby et al. | 73/159 |
| 4,965,450 A | | 10/1990 | Schiltz et al. | 250/303 |
| 5,159,829 A | | 11/1992 | Mayer et al. | 73/38 |
| 5,390,539 A | * | 2/1995 | Mayer | 73/38 |
| 6,119,506 A | | 9/2000 | Gibson et al. | 73/38 |
| 6,358,570 B1 | | 3/2002 | Affinito | 427/495 |
| 6,413,645 B1 | | 7/2002 | Graff et al. | 428/446 |
| 6,655,192 B2 | * | 12/2003 | Chavdar | 73/38 |
| 6,688,160 B2 | * | 2/2004 | Hackett, Jr. | 73/38 |
| 6,804,989 B2 | * | 10/2004 | Bujas et al. | 73/38 |
| 6,993,956 B2 | * | 2/2006 | Bouten et al. | 73/38 |
| 2002/0152800 A1 | * | 10/2002 | Bouten et al. | 73/38 |
| 2002/0162384 A1 | * | 11/2002 | Sharp et al. | 73/38 |
| 2003/0074954 A1 | | 4/2003 | Engle et al. | 73/38 |

* cited by examiner

*Primary Examiner*—Hezron Williams
*Assistant Examiner*—Ryan Christensen
(74) *Attorney, Agent, or Firm*—Fitch, Even, Tabin & Flannery

(57) ABSTRACT

Method and apparatus for testing ultralow moisture permeation through a sample such as a thin barrier film by exposing one surface of a sample to be tested for moisture permeation to a predetermined humidity of HTO. The HTO permeating therethrough is collected in a stream of dry gas, preferably methane, at a known very slow flow rate, and monitored for its radioactivity content. By very carefully sizing the respective chambers, continuously monitoring using a particularly sensitive device and appropriately converting the signals, accurate assessment of permeation rates even as low as very small fractions of a gram of water per square meter per day can be obtained. Ultralow oxygen permeation is alternatively measured using $^{14}CO$. Methods are also shown for measuring permeation that would occur through a perimeter seal and for measuring permeation which would result from gaseous entry into edge surfaces of a composite film.

18 Claims, 3 Drawing Sheets

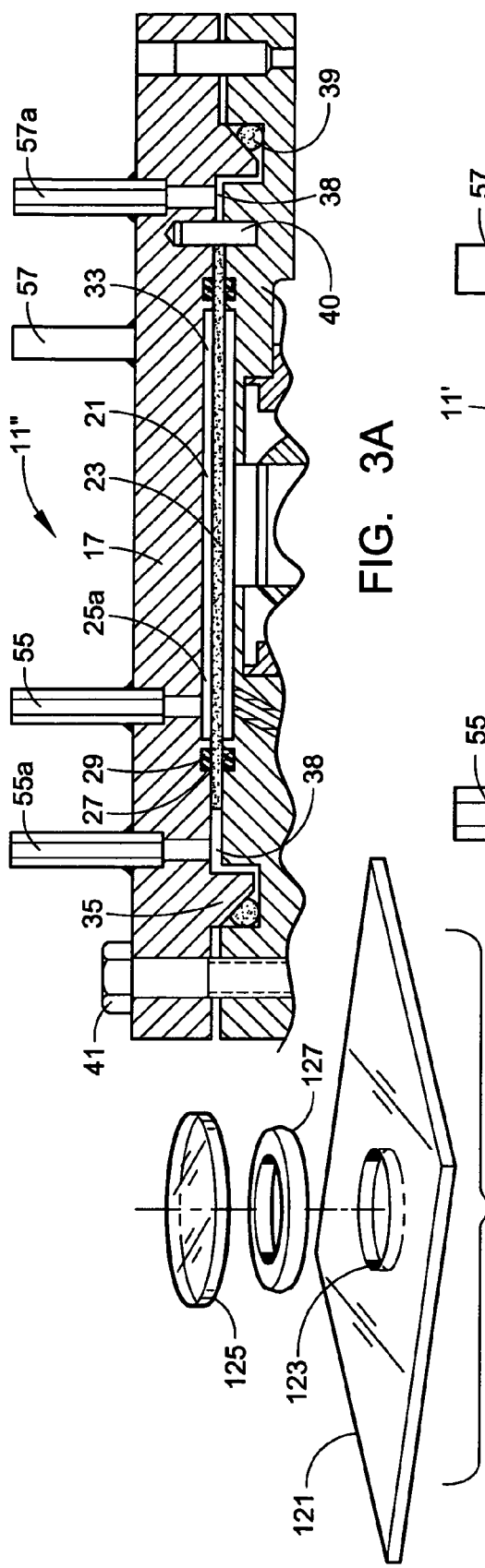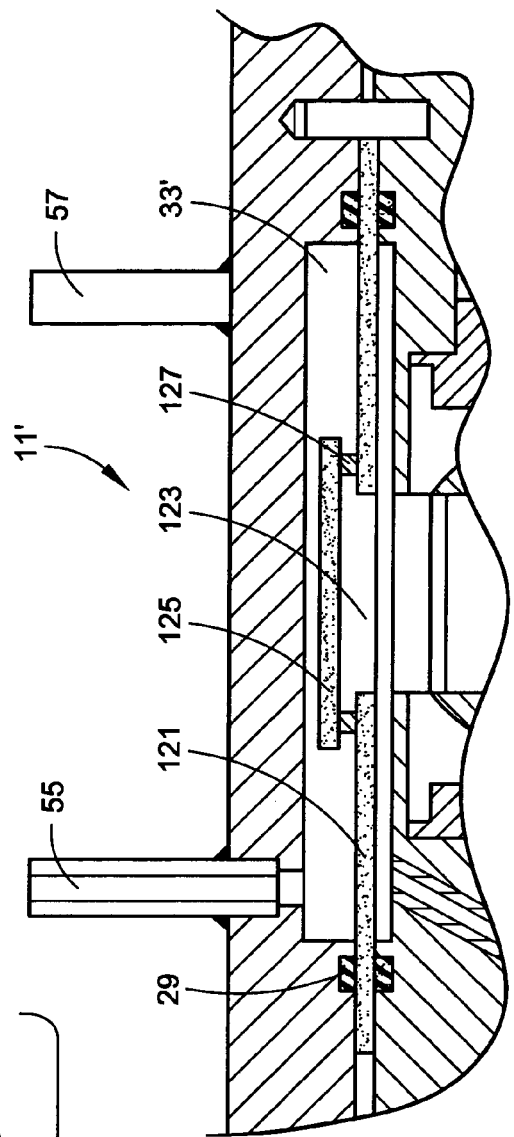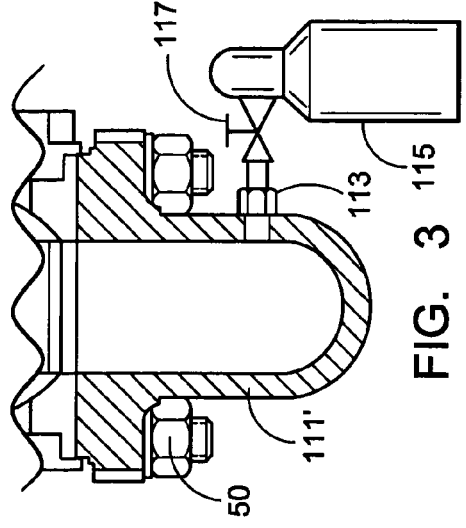

METHOD AND APPARATUS FOR MEASURING ULTRALOW PERMEATION

This invention was made with Government support under Army Contract No. DAAD19-02-3-0001. The Government may have certain rights in this invention.

The invention relates to methods and apparatus which allow the measurement of extremely low rates of permeation of water or oxygen, and more particularly to methods and apparatus for measuring an ultralow moisture permeation rate or oxygen permeation rate through an object, such as a sample polymer plastic film composite or other material.

BACKGROUND OF THE INVENTION

With the development of better and better barrier materials, generally from composites that include plastic films, it has now become very desirable to be able to precisely measure the rate of permeation through such barrier materials in order to properly evaluate them. As barrier materials have improved in their resistance to moisture and oxygen permeation, it has become clear that better, more sophisticated methods and apparatus are required to be able to accurately measure such lower and lower rates of permeation representative of barrier materials presently needed for commercial applications.

Gas permeability measuring devices have generally been known in the art, and some of these have been developed to serve the garment industry where fabrics that are highly resistant to water permeation are often desired. However, more recently, with the development of LCD's, LED's and OLED's, it has become important to develop barrier materials that have an extremely high resistance to moisture permeation and oxygen permeation. Although it has been shown scientifically that there is a relationship between the permeation of moisture and the permeation of oxygen through a barrier, so that by measuring the moisture permeation rate, an assessment can be obtained for the resistance of a barrier film or the like to the permeation of both moisture and oxygen, more precise measurements of oxygen permeation are often desired.

Because many present day products have been found to be highly sensitive to oxygen and moisture, often resulting in significant deterioration of the product, there has been a recent emphasis on developing better barrier materials. Products in the electronics fields, such as OLED's and LCD's, and certain pharmaceuticals are among products for which it is most important to resist such deterioration. The barrier materials that have been developed to protect such materials generally include multilayer composites made of polymeric films and thin layer inorganic materials, and the search has gone on for providing increasingly better multilayer, thin film barrier materials for this purpose. For example U.S. Pat. No. 6,413,645 entitled "Ultrabarrier Substrates" describes the problem and the search for more permeation-resistant materials. However, this patent states that oxygen and water vapor transmission rates even as high as 0.005 cc or $gm/m^2/day$ are below the detection limit of current industrial instrumentation.

To measure moisture permeation, efforts have been made to use the amount of change in weight of a suitable desiccant in a closed container where the object closing the container has its opposite face exposed to a humid atmosphere; however, the accuracy such apparatus has been frequently called into question. U.S. Pat. No. 3,580,067 illustrates another effort to use a desiccant in a closed container which is then placed in a chamber wherein a humidity of tritiated water vapor is maintained. The procedure involves batch analysis/counting where a plurality of sealed vials are needed, and the technician performing the procedure would be exposed to radioactive and toxic tritiated water vapor, each time a vial is removed and then handled. One must add a counting solution to dissolve the desiccant and facilitate counting on a liquid scintillation counter; the results are compared with a blank vial, containing the same amount of desiccant and counting solution. This provides a single point on a graph, and multiple points must be plotted before a measured water vapor transmission rate can be obtained. U.S. Pat. No. 4,663,969, issued May 12, 1987, discloses apparatus for testing water vapor transmission which employs a heated water bath; a solution containing a solute is employed along with an electrical conductivity measuring device to measure the change in concentration, which will be indicative of moisture permeation. However, it is felt that such an apparatus is not suitable to measure extremely low rates of moisture permeation.

U.S. Pat. No. 6,119,506 discloses an apparatus that is designed to allow measurement of mass transport. The flux of water vapor through a film or other object being measured is calculated by measuring results for exposure to a dry gas atmosphere, to a water-saturated atmosphere, and to atmospheres of different relative humidities; a computer program is used to determine transmission rate through the object being tested. Humidity probes are used to provide outlet signals that are indicative of the water vapor concentration in nitrogen streams that are flowed through a cell where such testing is occurring. In addition to being somewhat complicated, the apparatus is not felt to be well-suited to measuring extremely low moisture diffusion rates.

An instrument for determining the permeation rate of a gas, such as carbon dioxide, through a membrane is disclosed in U.S. Pat. No. 3,590,634, issued Jul. 6, 1971. The instrument flows a gas stream of constant concentration through an upstream chamber while flowing a carrier gas stream, such as helium, through a downstream chamber in order to measure permeation through a film which separates the two chambers. A thermal conductivity cell is provided to measure this characteristic of the carrier gas stream exiting at the downstream chamber, and an involved calibration system is required to interpret the data by comparing it with calibrations using a helium-carbon dioxide mixture of known composition. The arrangement is admittedly inappropriate for calculating very low permeation rates; it is stated that, when a continuous signal of noticeable magnitude is not being produced, it is necessary to isolate the permeation cell (by either halting or diverting the flow of the carrier gas) for a fixed time interval during which vapor is allowed to accumulate in the downstream chamber. After some predetermined time period, the accumulated vapor is allowed to be carried to the chamber, and the recorded peak and the area under the peak must then be graphically analyzed. The arrangement is clearly unsuitable for measuring ultralow permeation rates of oxygen.

In order to be able to effectively evaluate the performance of these new materials and other situations where highly effective barriers are involved, adequate test equipment is required for detecting moisture and/or oxygen permeation at these extremely low levels. Thus, more accurate apparatus and methods have been sought for measurement of such ultralow permeation rates.

SUMMARY OF THE INVENTION

It has now been found that a method and apparatus for measuring ultralow water permeation through a sample object, such as a composite film that includes a thin polymer layer, can be effectively created by utilizing a radioactive gas, such as tritiated water vapor (HTO) or carbon[14]monoxide ($^{14}CO$). By suitably mounting the sample object so as to provide controlled access to opposite surfaces of the barrier and by supplying HTO or $^{14}CO$ to its upstream surface, the permeating radioactive gas exiting downstream can be collected in a carefully controlled, dry carrier gas stream and monitored in a manner which can precisely determine even extremely low permeation rates through the sample. The method affords highly accurate measurement of ultralow permeation rates by uniformly controlling the humidity or other concentration at the upstream surface and by using a controlled, very low flow of dry carrier gas, preferably one having a matching molecular weight, downstream thereof in a chamber of only minimal size. Such a slowly flowing stream will collect all the radioactive permeated gas and carry it to a radiation monitor in an ionization chamber of minimal size where the permeation rate is then quickly and accurately calculated.

BRIEF DESCRIPTION OF THE DRAWINGS

FIG. 3 is a fragmentary view that shows an alternative supply subsystem to that of FIG. 2 adapted to measure for oxygen permeation.

FIG. 3a is another fragmentary view of the FIG. 2 mounting device which shows an alternative arrangement for monitoring for permeation flow in the plane of a thin film.

FIG. 4 is an exploded perspective view of an arrangement for measuring permeation through an adhesive seal.

FIG. 5 is fragmentary view, enlarged in size, of a portion of the mounting device of FIG. 2 with the arrangement of FIG. 4 installed.

DETAILED DESCRIPTION OF THE PREFERRED EMBODIMENTS

The invention provides a method and apparatus for accurately measuring even ultralow moisture or oxygen permeation through a thin film composite or other material having a high resistance to such penetration. As earlier mentioned, there has been substantial development of new materials, generally thin film composites, which provide high moisture and oxygen resistance for use as barriers for LCD's, LED's and OLED's that require such barrier protection to assure long term performance, particularly for the cathode components thereof, which are frequently manufactured of calcium and are particularly susceptible to degradation from moisture and attack by oxygen.

Figure 1:
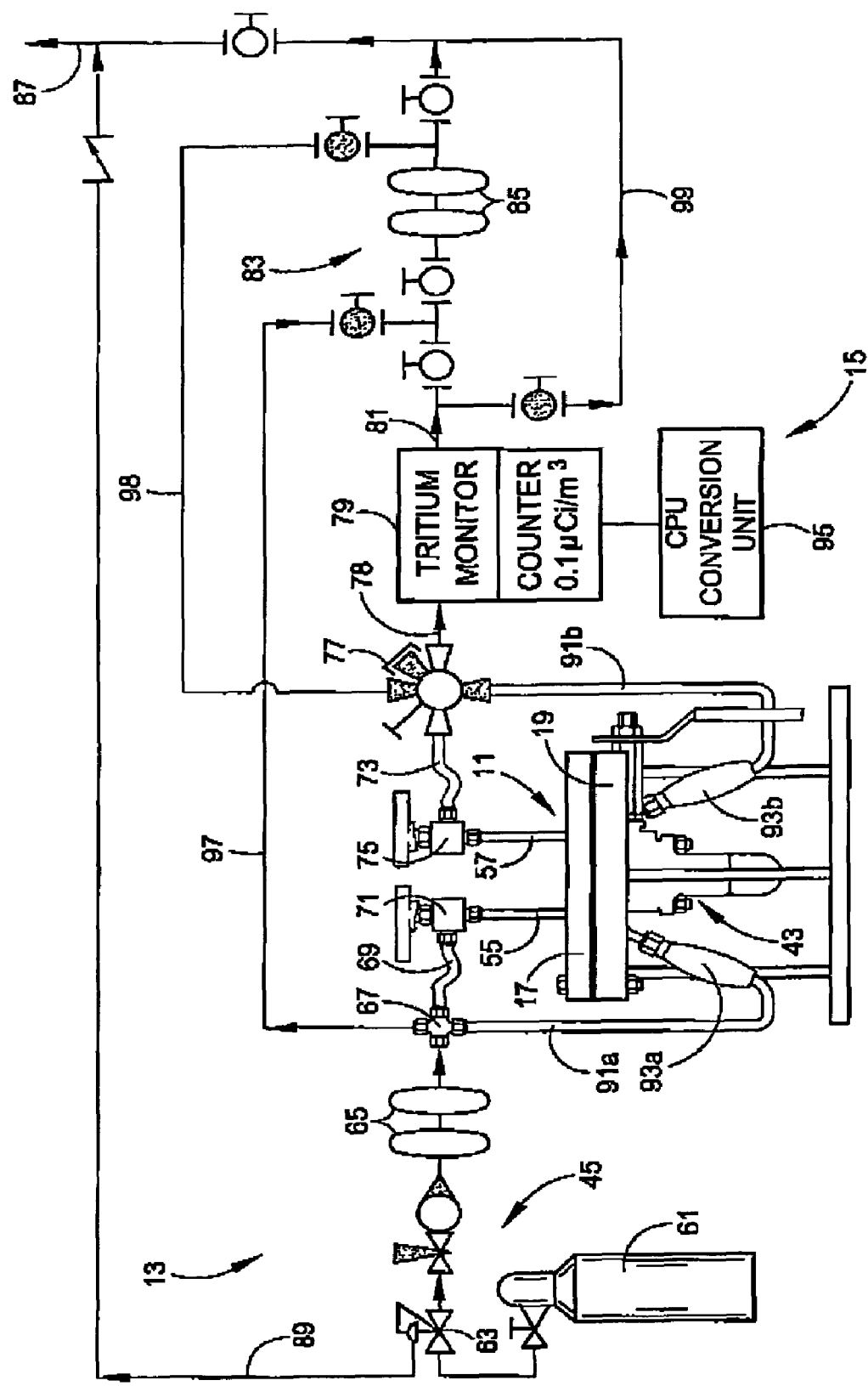
FIG. 1 is a schematic drawing showing apparatus for measuring ultralow rates of gaseous permeation through a sample, which apparatus embodies various features of the invention.

The apparatus shown in FIG. 1 includes a central mounting device 11 where a sample object for which permeation is to be measured is appropriately mounted so that a region of precise upstream surface area is directly exposed to an atmosphere of uniform composition so as to facilitate monitoring and accurately calculating permeation through the sample. Although the illustrated embodiment of the device 11 is designed to mount and measure permeation through a thin film, similar mounting devices could be constructed to handle similar objects of different shape and/or thickness; one such arrangement is depicted in FIG. 5.

Associated with the mounting device 11 are a system 13 for supplying controlled atmospheres upstream and downstream of the sample being tested, and a system 15 for monitoring the beta-particle radioactivity of a gaseous stream exiting the device 11 and interpreting the signals generated to calculate the permeation rate through the film or other sample at chat instant. The arrangement is such that the overall sensitivity is sufficient to detect and measure permeation rates of radioactive gaseous compounds of less than 0.0001 gm/m$^2$/day, for example, of moisture as low as $10^{-5}$ to $10^{-6}$ gm/m$^2$/day and of oxygen as low as $10^{-5}$ to $10^{-6}$ cc/m$^2$/day.

The illustrated mounting device 11 includes upper and lower halves or parts 17, 19. These two parts interface with each other to provide a central receptacle or chamber 21, which in the illustrated device is a shallow, generally square region designed for centrally mounting a square, flat, thin sample 23 for which permeation is to be determined. Accordingly, the central receptacle 21 is formed by a pair of facing shallow cavities 25a, 25b provided in the undersurface of the upper pan 17 and the top surface of the lower part 19, which are each only about 0.04 in. (0.1 cm) thick. Immediately surrounding each of these cavities is a groove 27 of square outline that defines the surface area of a film that will be exposed to the controlled atmosphere. The groove 27 is preferably rectangular or square in cross section and accommodates a sealing ring 29 of resilient material that extends outward past the respective surface Preferably sealing- or 0-rings 29 of square or rectangular cross section are placed in each of these grooves 27 so that, when the upper and lower parts 17, 19 are clamped or otherwise pressed together. the sealing rings 29 seal against the thin film 23 through which permeation is to be measured. As a result, the flat film then essentially splits the central receptacle 21 horizontally into a lower upstream subchamber 31 and an upper downstream subebamber 33. The square outline of the facing grooves is proportioned to expose a 3.5 inch (9 cm) scpaare of film composite. The size of the downstream subehainber 33 is minimized so as to have a volume of not more than about 10 cc. It has been found that, by minimizing the size of this chamber, by using only a very slow flow of dry gas, such as methane, as a carrier (Le., a flow of not greater than about 1.5 liters/hour) and by confining the beta-particle radiation monitor to a chamber of small volume, high sensitivity of measurement can be achieve.

Figures 2, 2A:
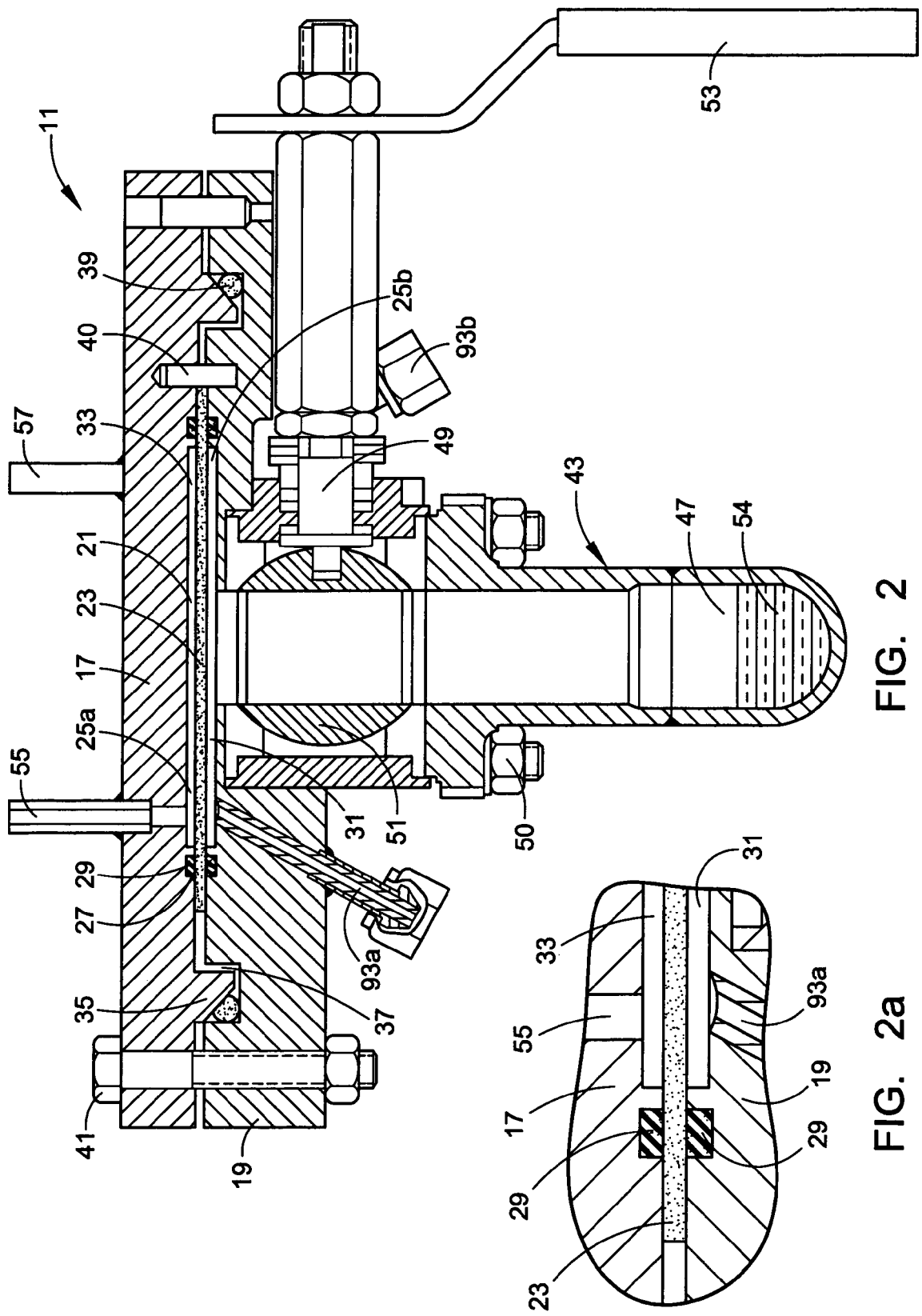
FIG. 2 is a sectional view through the mounting device shown in FIG. 1.
FIG. 2a is an enlarged view of a portion of the device of FIG. 2.

To align the upper and lower parts 17, 19 of the mounting device, one of the parts is provided with a protrusion and the opposite part is provided with a complementary receptacle to receive the protrusion. In the illustrated embodiment, the upper part 17 is provided with a continuous ridge 35 which is received in a facing groove 37 provided in the upper face of the lower part 19. The ridge 35 is preferably chamfered so as to accommodate an O-rings 39 to assure a tight fit and seal is obtained between the two halves once they are aligned as shown in FIG. 2. Moreover, this arrangement creates a sealed peripheral chamber 38 which is located intermediate the sealing rings 29 and the O-rings 39 to which advantage is taken in the alternative embodiment shown in FIG. 3A. One or more locator pins 40 may also be provided. The halves are pressed tightly together by the employment of a number of carriage bolts and nuts 41, which bolts are received in a plurality of vertical passageways located about the periphery of the mounting device 11. Other suitable methods of pressing or clamping the two halves together so that the sample film 23 being tested is tightly sealed between the facing sealing rings 29 could alternatively be used.

The overall gas supply system 13 illustrated in FIG. 1 includes a subsystem 43 for supplying an HTO atmosphere to the upstream subchamber 31 and a vapor collection subsystem 45 that includes an arrangement for supplying a flow of dry gas through the downstream subchamber 33 to collect the HTO that permeates through the sample 33 being tested. As an alternative for measuring oxygen permeation, a subsystem 43' is used which supplies $^{14}CO$ to the upstream subchamber 31 (see FIG. 3).

The HTO supply subsystem 43 includes an HTO reservoir 47 connected through a ball valve 49 to the upstream subchamber 31 that is formed in the lower half 19 of the mounting device. The ball valve 49 is bolted or otherwise suitably secured to the lower half, and the HTO reservoir 47 is connected in turn to the ball valve as by bolts 50. The ball valve 49 includes the usual spherical valve member 51 and a handle 53 for rotating the spherical ball member 90 degrees from the open position shown in FIG. 2 to a closed position where communication between the HTO reservoir 47 and the upstream subchamber 31 is totally broken.

A suitable source of HTO is placed in the reservoir 47 before it is installed on the mounting device. Preferably, a small quantity of liquid HTO is provided in the form of a pool 54; however, a crystalline salt that is saturated with HTO as its water of crystallization may instead be used. It is desired, at ambient temperature, that the closed chamber comprising the reservoir, ball valve and upstream subchamber 31 have a relative humidity of at least about 85%. Anhydrous potassium chloride will form KCl.2HTO when exposed to HTO, and by minimizing the volume of subchamber 31, a relative humidity of at least about 85% can be established throughout the upstream chamber within about 5 minutes with such a reservoir following opening the ball valve. Moreover, only a small amount of HTO vapor is lost when the upstream subchamber is purged before changing the film sample being tested. When 1 or 2 ccs of liquid HTO are used in the reservoir, as is preferred, such will provide close to 100% humidity. Moreover, this amount will provide sufficient HTO for test purposes for as long as one year under normal test conditions and usage, when the upstream chamber region between the ball valve member 51 and the film is no more than about 10 cc.

The upper part of 17 of the mounting device 11 contains a gas flow inlet passageway 55 leading into the subchamber 33 and a gas exit passageway 57 leaving an opposite region of the subchamber. The size of the mounting device and the subchambers can of course be varied; however, it has been found that using a device that exposes about 80 sq. cm of a thin film sample 23 to a controlled atmosphere provides adequate surface area so as to provide representative and accurate test readings for a thin film composite material engineered to serve as a highly resistant barrier layer. Moreover, minimization of the volumes of the subchambers 31, 33 is desired for the reasons discussed herein.

The overall gas supply system 13 includes a tank 61 of gas under pressure and the usual pressure regulator 63 to supply carrier gas to the mounting device at the appropriate pressure. Although various dry gases might be used, including argon, nitrogen, methane and dry air, it has been found that methane and argon have superior properties in the ionization chamber. For measuring moisture permeation, methane is preferred because the molecular weight of methane is very close to the molecular weight of water, as a result of which any potential stratification in the downstream subchamber at a low flow of gas therethrough is positively avoided. A test device such as this utilizing HTO, for general safety considerations, would normally be operated under a standard laboratory hood, and if methane is employed, the tank would normally also be located under the hood. If desired, a second cylinder of argon or the like might be also provided, with a 2-way valve to allow selection of either one for a particular test. For example, one may wish to use argon as a carrier gas when $O_2$ permeation resistance is being tested. Ultradry methane at a tank pressure of 2500 psi may be fed through the pressure regulator 63 to reduce its pressure to about 15 to 20 psia (i.e. just slightly above atmospheric pressure) for the testing/monitoring purposes of this invention. It is preferably passed first through a desiccant dryer 65 to remove any possible moisture that might be present and thus assure its ultradry condition.

The flow of methane leaving the desiccant dryer 65 enters a 4-way crossover connector 67, one leg 69 of which leads through a small ball valve 71 to the gas inlet passageway 55 to the downstream subchamber 33. An exit conduit 73 containing a ball valve 75 is connected to the gas exit passageway 57 from, and it leads to a 4-way connector 77 that contains a more sophisticated ball valve. This ball valve, 4-way connector always allows outward flow (as depicted in FIG. 1 by the arrowhead) through a conduit 78; rotation of the valve member connects the outlet line 78 to one of 3 conduits for purposes to be explained hereinafter. During normal testing, the carrier gas stream from conduit 73 is directed straight through the connector. Both of the ball valves 71, 75 are connected to the respective 4-way connectors by flexible tubing so as to allow the upper part 17 of the mounting device 11 to be removed to facilitate the removal and replacement of the sample film 23 being tested, as explained hereinafter.

During normal tescing, the ball valve connector 77 direct flows from the exit conduit 73 straight through to the conduit 78 leading to a monitoring chamber 79, which contains a beta-particle monitor, a commercial component that is disposed in a cylindrical chamber of small volume, i.e., preferably not greater than about 2 liters. Tritium emits beta particles, and the ionization detector in such a small chamber will effectively monitor the amount of radioactivity exhibited by the permeated tritium. It has been found that the minimization of the volume of the downstream subehainber, i.e., not more than 10 cc, and the use ofa very low flow of carrier gas, e.g. about 1 L of dry methane per hour, in combination with a small volume radiation monitoring chamber, e.g. about 2 liters, provide sufficient sensitivity to be able to achieve measurement levels less than 0.0001 $gm/m^2/day$, e.g., as low as about $10^{-6}$ to $10^{-5}$ $gm/m^2/day$. The ionization detector in the chamber 79 creates signals in response to the beta particle radiation and sends these signals to an interconnected counter which in turn sends signals to a CPU conversion unit 95. Such a detector in this small volume cylindrical chamber is effective to detect an amaunt of radiation as low as about 0.1 microcurie per $m^3$ and of course, the size of the chamber is a very small fraction of a cubic meter. The signal processing is described hereinbelow, An outlet 81 from the opposite or exit end of the cylindrical radiation monitoring chamber 97 leads to a conduit network 83 that includes a desiccant dryer 85 which will remove and accumulate all HTO that permeated during the test and found its way into the carrier gas flow through the downstream subehamber 33 of the mounting device 11.

Then the methane, stripped of all its radioactivity in the desiccant dryer 85, is vented through a suitable vent line 87. The overall gas supply network 13 also includes a second conduit 89 leading from the pressure regulator 63 to the vent line 87 through a check valve which serves as a safety bypass should, for some unknown reason, undesired high gas pressure reach the downstream side of regulator.

Lower conduits 91a and 91b lead, respectively, from the first crossover 67 and to the second valved crossover 77, and they are connected to a pair of ports 93a, 93b that lead to and from the subchamber 31 on the upstream side of the sample being tested. This arrangement is provided for purging the upstream subchamber of any residual radioactive gas preparatory to changing the sample 23 that is to be tested. To prepare to change the sample, the ball valve 49 is closed, and then a purge flow of gas is caused to sequentially flow through the subchambers 31 and 33. Initial flow is through the upstream subchamber 31 which is accomplished by setting the valved connector 77 to interconnect the conduit 91b to the conduit 78; this causes the methane flow from the pressure regulator 63 to become a purge flow through the upstream subchamber 31 via the conduits 91a, 91b. Such flow is continued until the radiation monitor 79 indicates there is no longer any radioactivity present in gas stream that is exiting from the subchamber 31 of the mounting device. After the radiation monitor 79 indicates the upstream chamber 31 has been purged, the downstream chamber 33 is purged by flowing carrier gas in its normal pattern.

In addition, the conduit network 83 includes a bypass conduit 97 incorporating a suitable valve which allows a purge flow of dry gas to short circuit the test device 11 and be directed into the network downstream of the radiation chamber 79 so it flows through the dryer 85 and then into a side flow conduit 98 containing a suitable off/on valve that routes the flow exiting the dryer 85 to the connector 77. By so rotating the valve in the connector 77, the flow from the side conduit 98 is sent through the conduit 78 to the radiation chamber. Such a purge flow pattern is used before replacement of conduits or components in this region is undertaken to assure that there is no residual radioactivity in the system itself or to ascertain that the dryer 85 is effectively sequestering all of the HTO. By opening a valve in a second bypass conduit 99, this flow path of purge gas originating in the bypass conduit 97 is sequentially through the dryer 85, then the radiation monitor 79 and then into the conduit 99 leading to the vent 87.

The radiation monitor 79 is electrically connected to the conversion unit 95 which can include a CPU that is programmed to make calculations from the signals received from the radioactivity monitor that are indicative of amount of permeated HTO collected and carried by the flow of methane gas at any time. From such readings during a given period of time, and the knowledge of the rate of gas flow and the length of time during which the test was carried out, the unit 95 is appropriately calibrated and programmed to provide a cumulative readout in the form of the number of grams of water per square meter per day which are permeating through the sample 23 being tested which is being exposed to a controlled humidity under essentially ambient conditions. If desired, the HTO supply system can include a heater so as to test a film at a higher temperature, i.e. 38° C., should such be desired.

As an example of the overall operation, an appropriate sized sample 23 of a barrier film to be tested is carefully installed in the mounting device 11 so that it rests upon the upper surface of the protruding square cross-section O-rings 29 in the lower half 19 of the device, as best seen in FIG. 2a.

The upper half 17 is then carefully set in place, and the carriage bolts and nuts 41 installed so as to clamp the film 23 securely between the mating sealing rings 29 and to seal the central receptacle about its periphery by the O-rings 39. Once the device is closed, a purge flow of dry methane is sent through the downstream subchamber 33 to rid the chamber of any humidity and other residuals; such flow is directed through the radiation monitoring chamber and continued until a stable baseline is recorded which indicates the subchamber has been purged. Following this purging, a slow flow of dry methane is passed through the upstream chamber 31 to similarly purge it. At such time the slow flow of methane is halted, and the ball-valve 49 is opened, causing HTO vapor from the underlying reservoir 47 to flow into the upstream chamber 31. The upstream subchamber is quickly filled with a uniform HTO humidity; in just one minute, the subchamber is about 50% saturated. The thin polymeric film layer fairly rapidly saturates with HTO. At this time, a slow uniform flow of dry methane is passed through the downstream subchamber and continued at a rate of about 1 liter/hour. When it is noticed that some radiation above baseline is being detected, the test is considered to have been begun, and a such flow of dry methane at, for example, about 1 liter per hour is continuously maintained through the downstream subchamber 33 and then through the radiation monitor 79. If desired, a volumetric flow monitor (not shown) may be included to assure precision is being achieved. As previously indicated, the methane/HTO leaving the radiation monitor 79 passes through the final desiccant dryer 85, which absorbs all the collected HTO exiting the radiation monitor and allows only totally dry, non-radioactive methane to flow out the vent 87. The signals generated by the counter at the radiation monitor 79 are, for the duration of the test, continuously fed to the conversion unit 95 which is programmed to calculate a moisture permeation rate in desired terms, as for example, grams of water per square meter of surface area per day. The unit 95 will indicate the current permeation rate being detected as well as the cumulative average rate over the entire length of the test, or any other period desired, as the rates being monitored are being continuously recorded.

As previously mentioned, when the test has been satisfactorily completed, the ball valve 49 is closed, and the upstream and downstream subchambers 31, 33 are sequentially purged of HTO by flowing dry methane therethrough until no radiation is still being detected by the monitor Then the mounting device 11 is opened, and the sample 23 is removed and replaced with the next one to be tested.

Depicted in FIG. 3 is a fragmentary view showing an alternative subsystem 43' that is used instead of the reservoir of HTO in order to specifically test for oxygen permeation. The size of the oxygen ($O_2$) molecule is very close to the size of the carbon monoxide (CO) molecule, and the molecular weights are likewise quite close. Therefore, it has been determined that the use of carbon$^{14}$monoxide can provide a very close approximation, from the standpoint of vapor permeation through a thin barrier film or other sample, of the permeation of $O_2$. Accordingly, testing specifically for oxygen permeation is carried out by using radioactive $^{14}CO$, instead of using a reservoir of HTO, and a simple closure 111 which contains a connector 113 to mate with a fitting at the end of a supply conduit attached to a source of carbon monoxide is employed. The closure 111 is bolted to the test device in the region below the ball valve 49, as depicted in FIG. 3. A cylinder 115 of carbon$^{14}$monoxide is employed, along with a pressure regulator 117 which reduces the pressure at the outlet from the tank to a value just slightly above ambient pressure, e.g. to about 15 psia. Once connection is made to the test device, carbon monoxide will fill the region below the ball valve member 51, and the test will proceed in substantially the same manner as it was carried out when the region below the ball valve member was filled with an atmosphere having a high HTO humidity. Once the valve member 51 is rotated to the open position, carbon monoxide will quickly permeate the upstream subchamber and begin to permeate through the sample being tested, e.g. the thin film 23; the radioactive gas which permeates is again collected by the extremely slow flow of argon, that is used in place of methane, through the downstream subchamber 33 and carried to the radiation chamber. Although at about ambient temperature there is no chemical reaction between methane and carbon monoxide, argon is preferably employed as an alternative carrier gas because its molecular weight closely matches that of CO.

Carbon monoxide is also a beta-particle emitter; therefore, the same radiation monitoring device 79 as described earlier can be employed. Instead of employing a desiccant in the absorption chamber 85, a metal alloy getter material, such as those disclosed in U.S. Pat. No. 5,866,978 may be employed, and the carrier gas stream exiting the radiation chamber is flowed through a pack containing a high surface area alloy material to adsorb the carbon monoxide instead of the desiccant drier 85. The remainder of the carrier gas stream proceeds to vent to the atmosphere as previously described. Accordingly, it can be seen that essentially the same measuring device is useful to measure directly either for moisture permeation or for oxygen permeation.

Shown in FIGS. 4 and 5 is an arrangement for testing a different type of sample for moisture or oxygen permeation using the system and apparatus of FIG. 1.

Glass plates have long been used as protection for OLEDs and the like, as glass is an excellent barrier to both oxygen and moisture. In many cell phones, for example, a pair of thin glass plates are used to sandwich an OLED or other light-emitting display. However, in such an arrangement, a perimeter seal is necessary to prevent moisture and oxygen from otherwise entering from the side edges of the assembled arrangement. As a result, it has become important to be able to determine the effectiveness of a perimeter seal, which will normally be a line or bead of adhesive that completely encircles the usually rectangular perimeter of the device. Whereas the thickness of the seal is determined by the thickness of the light emitting display material being sandwiched between the two plates, the width of the line of adhesive is variable, as is of course the chemical/physical composition of the adhesive itself that is used to create the seal. Accordingly, it is important to monitor the effectiveness of a prospective adhesive seal in order to determine not only the appropriate adhesive to use, but the width of the bead or line of adhesive that should used to effectively seal, for example, a pair of thin glass plates.

FIGS. 4 and 5 depict an arrangement that can be employed for such testing using the system and the mounting device 11 previously described. Depending upon the thickness of the glass plates, it may be desired to slightly enlarge the depth of the downstream subchamber (see subchamber 33' in device 11'; however, in many instances, such should not be necessary. For this testing arrangement, a thin glass plate about 0.15 cm thick is provided that has essentially the same dimensions as the standard composite film sample that is tested, namely a flat plate about 3.5 inches square. A large opening 123 is created centrally within the glass plate, which in the illustrated arrangement is an oval hole. A thin glass disk 125, which may be of the same material of the plate, is provided. This disk 125 can, for instance, be a flat plate of circular shape having a diameter of about 2.5 inches; it will need to be larger in surface area than the hole 123 so as to accommodate a seal 127 between the glass disk and the plate around the hole, using a continuous line of adhesive of the same thickness as will be intended to be used in the perimeter seal of the cell phone or other display unit. The proportions are chosen to be such that such a line of adhesive 127 will have a defined length, for example, the circumference of a circular bead of adhesive sealing the disk to the plate may be the same length as the perimeter of the display unit of interest. The line of adhesive 127 should be uniform in width and have the specific width that is felt to be adequate for the desired barrier protection so that the thickness, the width and the length of the line of adhesive is the same as, or in a desired proportion to, that which will be used in the commercial device.

When the assembly of plate and disk is mounted in the mounting means 11', and the system is ready for testing, the ball valve is opened so that the region on the upstream side of the circular disk 125 (the surface facing the plate) will be filled with the humid HTO atmosphere which enters this region through the large oval hole 123.

Thus, this humid atmosphere will be in contact with the upstream, i.e., interior, edge of the circular line of adhesive 127. Accordingly, permeation into and slowly through the line of adhesive will occur, the rate of course depending upon the physical characteristics of the adhesive material; the permeating HTO will be collected by the slow flow of carrier gas through the subchamber 33' and carried to the radiation monitor as explained hereinbefore. Thus, the apparatus and system described hereinbefore with regard to testing the barrier properties of a thin film is also useful for testing the barrier properties of an edge seal in an accurate manner and in similar instances where the determination of even ultralow rates of permeation of moisture or oxygen through such a seal is of significant importance.

Although it is expected that the primary entry flow of moisture or oxygen that permeates through a composite barrier film will be from the exposed region bordering the large surface area of the barrier film that is in contact with the atmosphere, it has come to the attention of those working in this area that there may also be entry flow through the edge regions of the polymeric film layers in the composite film. It is presently considered important to be able to test a composite film to determine the significance of such permeation via entry through edge surfaces. In this respect, it is been found that a simple modification to the system and apparatus illustrated and described with respect to FIGS. 1 and 2 can be made to facilitate such testing.

Illustrated in FIG. 3A is a mounting device 11" wherein a second gas inlet passageway 55a and a second gas exit passageway 57a have been added to the upper half 17. These two passageways provide for an alternative flow of carrier gas, i.e., through the peripheral region 38 that surrounds the thin film sample that is mounted in the device for permeation testing. As earlier indicated, this peripheral chamber encompasses the region between the sealing rings 29 and the O-rings 39.

In operation, the inlet gas passageway 55a would be connected via a valved line to a tee (not shown) in the line 69 between the 4-way connector 67 and the inlet passageway 55. Similarly, the exit passageway 57a would be connected via a line containing a valve to a tee (not shown) placed in the line 73 between the valve 75 and the valved connectors 77.

With this arrangement, once the film sample has been tested for the rate of permeation directly across the upstream surface and out the downstream surface as hereinbefore described, the valves 71 and 75 could be closed and the valves opened in the lines leading to the passageways 55*a*, 57*a*. This would result in the slow flow of carrier gas thereafter being through the peripheral chamber 38. Once the system stabilized, it would provide an accurate reading of the amount of permeation from the saturated polymeric film out the peripheral edge of the square section of composite film being tested. Although such flow would be in the opposite direction to that of interest from the standpoint of a barrier film, it should be understood that this flow would be representative of the rate at which moisture or oxygen entering a similar film through its edge surfaces would find its way to and permeate from the surface adjacent which the light-emitting device is disposed. Accordingly, with this simple modification, an accurate arrangement is provided for being able to accurately assess ultralow permeation flow in a composite film barrier material that would result from entry through edges of such film.

Although the invention has been described with regard to certain preferred embodiments which constitute the best mode presently known to the inventors to carry out the invention, it should be understood that various changes and modifications as would be obvious to one having ordinary skill in this art can be made without departing from the scope of the invention which is defined by the claims that are appended hereto. Even though the primary working example is directed to testing improved barrier materials suitable for the formation of a flexible OLED or the like, it should be understood that other materials may alternatively be tested by appropriately altering the mounting device should such be found necessary. Likewise, if desired, both sets of valves could be opened and the permeation of radioactive gas exiting the downstream surface and the edge surfaces of a film sample could be simultaneously collected and monitored. Disclosures of all previously enumerated U.S. patents are expressly incorporated herein by reference. Particular features of the invention are enumerated in the claims which follow.

The invention claimed is:

1. A method for measuring ultralow permeation through an adhesive perimeter using a radioactive compound, which method comprises the steps of:
   mounting a line of adhesive through which permeation is to be measured between two plates so as to provide controlled access to an upstream surface of the line of adhesive in a first chamber and to a downstream surface thereof in a second chamber, wherein said second downstream chamber has a volume of not greater than about 10 cm$^3$,
   supplying a radioactive gas from a source to be in contact with the upstream surface of the line of adhesive in the first chamber,
   collecting radioactive gas permeating from the downstream surface of the sample by circulating a very slow flow of dry carrier gas at a rate of not greater than about 1.5 liter per hour through the second chamber to provide a radioactive stream,
   flowing said radioactive stream from said second chamber to an entrance to an ionic chamber not greater than about 2 liters in volume containing a beta-particle radiation monitor,
   continuously monitoring said stream for beta particle radioactivity and generating signals, and
   receiving signals from said radiation monitor in conversion means and converting the signals to calculate the permeation rate through the sample at that moment, whereby the sensitivity of the method allows measurement of permeation of radioactive gaseous compounds through lines of adhesive that have barrier properties which permit permeation at rates of less than 0.0001 gm/sq.m/day.

2. The method for measuring permeation according to claim 1 wherein said radioactive gas is tritiated water vapor (HTO).

3. The method for measuring permeation according to claim 2 wherein a relative humidity of HTO between about 85% and 100% is supplied to the first chamber throughout the entire test period for the sample.

4. The method for measuring permeation according to claim 1 wherein said radioactive gas is HTO and said carrier gas is dry methane.

5. The method for measuring permeation according to claim 1 wherein said radioactive gas is carbon$^{14}$ monoxide (14CO).

6. The method for measuring permeation according to claim 5 wherein said carrier gas is dry argon.

7. The method for measuring permeation according to claim 1 wherein said carrier gas enters said second chamber at a pressure just sufficient to maintain the desired very slow flow and is vented to the atmosphere through an absorption device which removes all of said radioactive compound from said carrier gas stream.

8. The method for measuring permeation according to claim 7 wherein said carrier gas enters at a pressure of not greater than about 1.1 atm.

9. A method for testing a perimeter seal including adhesive material for ultralow permeation therethrough using a radioactive compound, which method comprises the steps of:
   providing two plates, one of which has an opening therethrough which is spaced from the edges thereof, and assembling said plates so their facing surfaces are spaced substantially equidistant to each other by a continuous seal that includes adhesive material and encircles said opening,
   mounting said assembly so as to provide controlled access to said plate containing the opening in a first chamber and to the other plate in a second chamber,
   supplying a radioactive gas to the first chamber from a source so as to fill the region between said two plates and thus be in contact with an upstream surface of the continuous seal,
   collecting radioactive gas permeating from the downstream surface of the perimeter seal by circulating a very slow flow of dry carrier gas at a rate of not greater than about 1.5 liters per hour through the second chamber to provide a collection stream,
   flowing said radioactive collection stream from said second chamber to an entrance to an ionization chamber containing a beta-particle radiation monitor,
   continuously monitoring said stream for beta-particle radioactivity and generating signals, and
   receiving signals from said radiation monitor in conversion means and converting the signals to calculate the permeation rate through the mounted perimeter seal at that moment.

10. The method for testing for permeation according to claim 9 wherein said radioactive gas is either tritiated water vapor (HTO) or $^{14}$CO.

11. Apparatus for measuring ultralow permeation through adhesive material, which apparatus comprises:
- a first flat plate having an opening which extends therethrough,
- means for mounting a second flat plate having an area greater than said opening spaced from a downstream surface of said first flat plate by a line of adhesive of defined thickness and width, which adhesive line completely encircles said opening and creates a seal between said plates through which permeation is to be measured,
- a first chamber in communication with an upstream surface of said first plate,
- a second chamber in communication with the downstream surface thereof, said second downstream chamber having a volume not greater than about 10 cm$^3$,
- means for supplying a radioactive gas to the first chamber where it will be in contact with the line of adhesive between said plates,
- means for circulating a slow flow of carrier gas through the second chamber to provide a stream containing the radioactive gas permeating through the line of adhesive,
- conduit means for flowing said stream from said second chamber to an ionic chamber that contains a radiation monitor for continuously monitoring said stream for beta particle radioactivity and for creating signals indicative of radioactivity, said ionic chamber having a volume not greater than about 2 liters, and
- conversion means for receiving signals from said radiation monitor and converting the signals to calculate the permeation rate through the sample at that moment, whereby the sensitivity is such as to detect permeation of radioactive gaseous compounds through a sample line of adhesive that has baffler properties which permit permeation at a rate of less than 0.0001 gm/m$^2$/day.

12. A method for measuring ultralow permeation through a sample using a radioactive compound, which method comprises the steps of:
- mounting a sample through which permeation is to be measured so as to provide controlled access to an upstream surface of the sample in a first chamber and to a downstream surface thereof in a second chamber, wherein said second downstream chamber has a volume of not greater than about 10cm$^3$,
- supplying carbon$^{14}$ monoxide ($^{14}$CO) from a source so as to be in contact with the upstream surface of the sample in the first chamber,
- collecting $^{14}$CO permeating from the downstream surface of the sample by circulating a very slow flow of dry carrier gas at a rate of not greater than about 1.5 liter per hour through the second chamber to provide a radioactive stream,
- flowing said radioactive stream from said second chamber to an entrance to an ionic chamber not greater than about 2 liters in volume containing a beta-particle radiation monitor,
- continuously monitoring said stream for beta particle radioactivity and generating signals, and
- receiving signals from said radiation monitor in conversion means and converting the signals to calculate the permeation rate through the sample at that moment, whereby the sensitivity of the method allows measurement of permeation of $^{14}$CO through samples that have baffler properties which permit permeation at rates of less than 0.0001 gm/sq.m/day.

13. The method for measuring permeation according to claim 12 wherein $^{14}$CO is supplied to the first chamber at a pressure slightly above ambient.

14. The method for measuring permeation according to claim 12 wherein said carrier gas is dry argon.

15. The method for measuring permeation according to claim 12 wherein said carrier gas enters said second chamber at a pressure just sufficient to maintain the desired very slow flow and is vented to the atmosphere through an absorption device which removes all of said 14CO from said carrier gas stream.

16. The method for measuring permeation according to claim 15 wherein said carrier gas enters at a pressure of not greater than about 1.1 atm.

17. The method for measuring permeation according to claim 12 wherein said sample is a polymeric film.

18. The method for measuring permeation according to claim 12 wherein said sample is line of adhesive of uniform width disposed between two flat plates.

* * * * *

UNITED STATES PATENT AND TRADEMARK OFFICE
CERTIFICATE OF CORRECTION

PATENT NO. : 7,178,384 B2
APPLICATION NO. : 10/772765
DATED : February 20, 2007
INVENTOR(S) : Bujas et al.

It is certified that error appears in the above-identified patent and that said Letters Patent is hereby corrected as shown below:

In the CLAIMS:

Claim 5, column 12, line 21, change "(14CO)" to --($^{14}$CO)--.

Claim 11, column 13, line 35, delete "baffler" and insert --barrier--.

Claim 12, column 14, line 22, delete "baffler" and insert --barrier--.

Claim 15, column 14, line 33, change "(14CO)" to --$^{14}$CO--.

Signed and Sealed this

Third Day of July, 2007

JON W. DUDAS
*Director of the United States Patent and Trademark Office*